US009974119B1

(12) United States Patent
Qasem

(10) Patent No.: US 9,974,119 B1
(45) Date of Patent: May 15, 2018

(54) PORTABLE INCENSE BURNER

(71) Applicant: Sadeq Ahmad Qasem, Adan (KW)

(72) Inventor: Sadeq Ahmad Qasem, Adan (KW)

( * ) Notice: Subject to any disclaimer, the term of this patent is extended or adjusted under 35 U.S.C. 154(b) by 0 days. days.

(21) Appl. No.: 15/413,423

(22) Filed: Jan. 24, 2017

(51) Int. Cl.
*H05B 1/02* (2006.01)
(52) U.S. Cl.
CPC .................. *H05B 1/0288* (2013.01)
(58) Field of Classification Search
CPC .................................................. H05B 1/0288
See application file for complete search history.

(56) References Cited

U.S. PATENT DOCUMENTS

| 3,058,178 A | 10/1962 | Campagna | |
|---|---|---|---|
| 3,366,775 A * | 1/1968 | Mycue | H05B 3/00 128/203.27 |
| 6,183,200 B1 * | 2/2001 | Chang | A01M 29/12 415/121.2 |
| 2004/0136888 A1 * | 7/2004 | Shimizu | A61L 9/03 422/305 |
| 2011/0097242 A1 | 4/2011 | Al-Mahnna | |

FOREIGN PATENT DOCUMENTS

| CN | 203538623 | * | 4/2014 |
|---|---|---|---|
| CN | 204483382 | * | 7/2015 |

OTHER PUBLICATIONS

Wang. CN 203538623. English Machine Translation.*
Cao et al. CN 204483382. English Machine Translation.*

* cited by examiner

*Primary Examiner* — Donald R Spamer

(57) ABSTRACT

A self-contained incense burner shaped a hairdryer for safely holding, igniting and burning incense. The portable incense burner shaped a hairdryer is going to heat the incense with a certain temperature in order to help the user to direct the smoke flow in the exact direction of the nozzle using the fan thrust. The self-contained incense burner shaped a hairdryer has a small as pocket size and is portable without any wires to enhance the mobility of the users and the way of using incense.

14 Claims, 3 Drawing Sheets

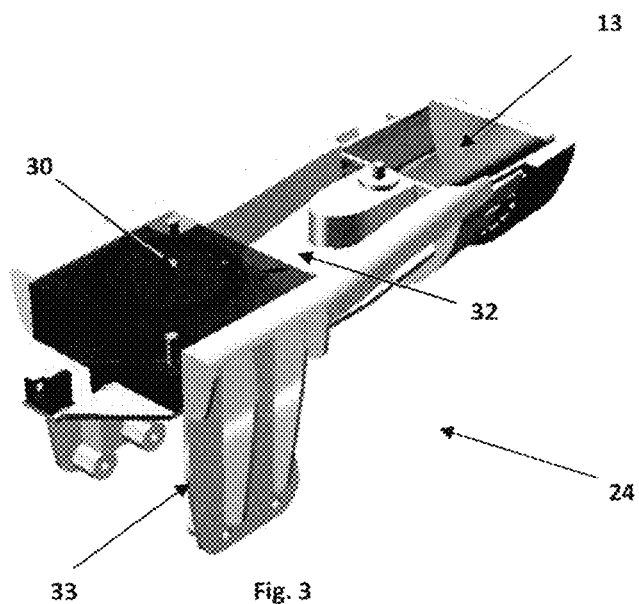
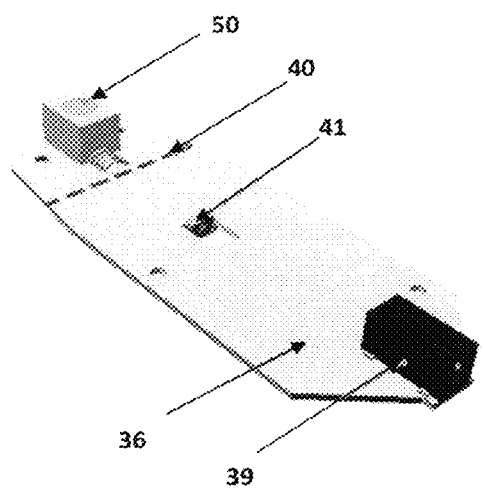
Fig. 3
Fig. 4

PORTABLE INCENSE BURNER

BACKGROUND OF THE INVENTION

1. Field of the Invention

The present invention relates generally Portable incense burner and more particularly to a self-contained incense burner shaped a hairdryer for safely holding, igniting and burning incense.

2. Description of the Related Art

Incense burners are well known and have been in use for many years. Burners of various designs are appropriate for different applications ranging from religious services to a device for killing flying insects and/or dispensing a pleasant aroma.

For example, a U.S. Pat. No. 3,058,178 of Campagna relates to a portable incense burner that is particularly well suited for use in religious ceremonies. Early burners placed burning charcoals in a portable receptacle provided with holes in the wall to permit air to pass, to the charcoal to keep it burning and to permit the escape of incensed fumes. Incense is placed over the burning coal to produce the fumes. In order to overcome a problem associated with receptacles becoming very hot on the outer surface, and the inconvenience of refilling at an inconvenient time, Campagna teaches the use of an electrical socket and a thermostat to control the heat applied to the incense.

A more recent patent US2011097242 of Khaled relates to an incense burner and storage device in accordance with the present invention includes a lower housing with a base and a storage compartment for storing incense, charcoal and the like and a plurality of small disposal cigarette lighters. The incense burner and storage device also includes an upper housing and an upwardly extending column having upper and lower portions fixed to the base and extending upwardly therefrom for supporting the upper housing above and at a small distance from the lower housing. The upper housing includes a ceramic support for charcoal and incense, an ashtray for collecting ashes remaining alter the charcoal and incense have been burned. The ashtray is also rotatable about a vertical axis between a loading position and a burning position. The ashtray also includes a perforated screen-like bottom that allows a flame to pass there through. An important feature of the present invention resides in a flame supporting means namely a disposal cigarette lighter for heating and igniting the charcoal that is pivotally mounted within the column and rotatable about a horizontal axis outside of the column for removal sand replacement of the igniter. Another important feature of the present device resides in the adjustment mechanism that is fixed to one side of the upper portion of the column and allows the charcoal and incense support to be raised or lowered with respect to the cigarette lighter Notwithstanding the above it is presently believed that there is a potential demand and a commercial market for an incense burner and storage device in accordance with the present invention.

SUMMARY OF THE INVENTION

The present invention relates generally portable incense burner and more particularly to a self-contained incense burner shaped a hairdryer for safely holding, igniting and burning incense.

The portable incense burner shaped a hairdryer is going to heat the incense with a certain temperature in order to help the user to direct the smoke flow in the exact direction of the nozzle using the fan thrust. The self-contained incense burner shaped a hairdryer has a small as pocket size and is portable without any wires to enhance the mobility of the users and the way of using incense.

These and other features of the present invention will become readily apparent upon further review of the following specification and drawings.

BRIEF DESCRIPTION OF THE DRAWINGS

FIG. 3 is a detailed perspective view of main circuit housing according to the present invention.

FIG. 4 is a more detailed perspective view of interior design printed circuit board PCB according to the present invention.

Similar reference characters denote corresponding features consistently throughout the attached drawings.

DETAILED DESCRIPTION OF THE PREFERRED EMBODIMENTS

The present invention relates generally Portable incense burner shaped a hairdryer.

Figure 1:
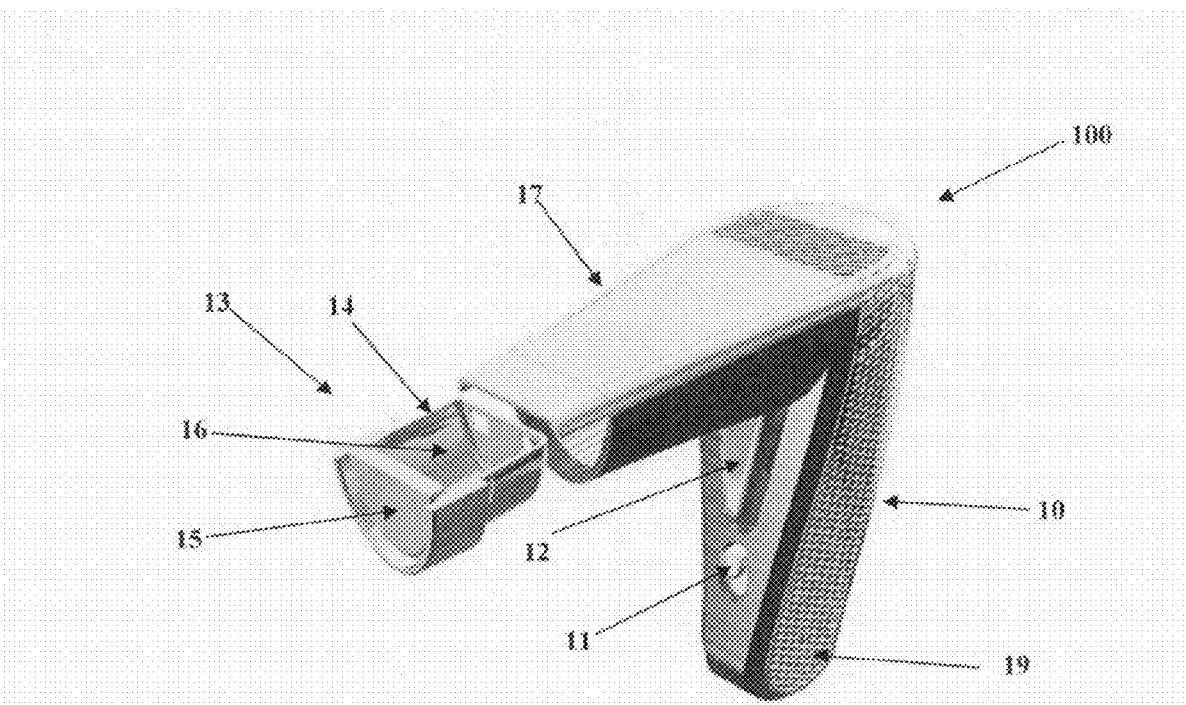
FIG. 1 is an environmental, perspective view of the portable incense burner.
Figure 2:
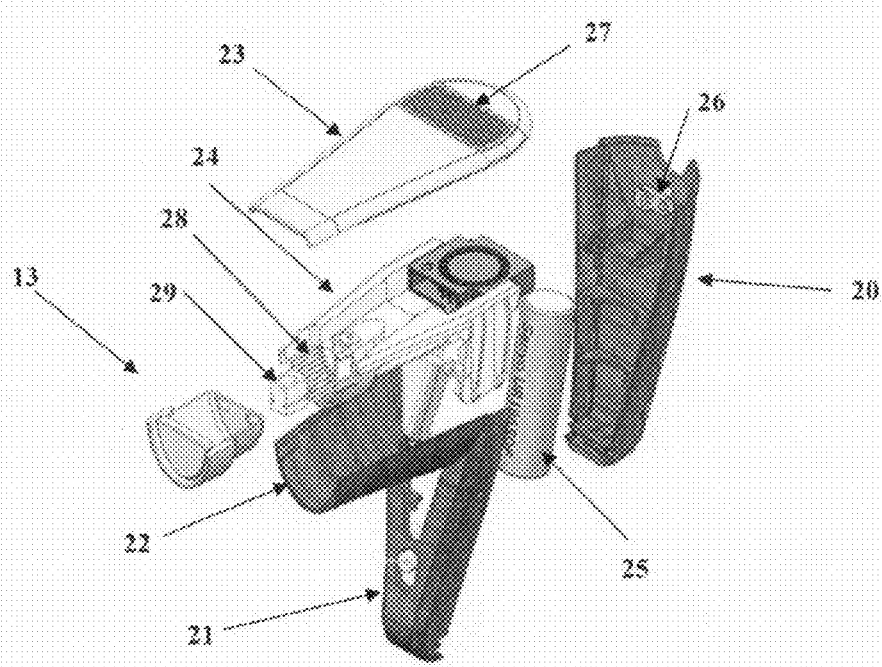
FIG. 2 is a detailed perspective view of portable incense burner.
Figure 5:
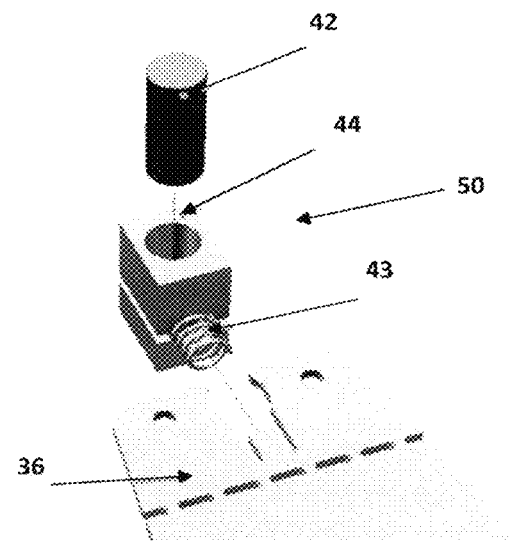
FIG. 5 is a perspective view of the heater elements details according to the present invention.
Figure 6:
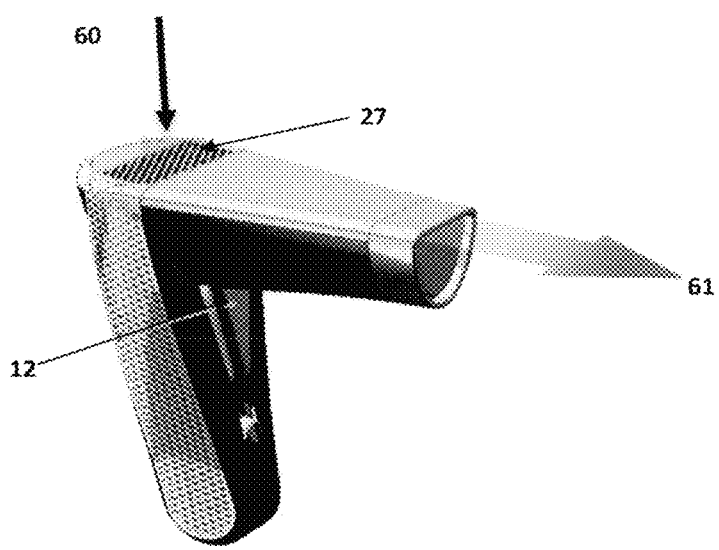
FIG. 6 is a perspective view of the portable censer burner operation showing air flow direction.

Referring to FIGS. 1 and 2 which describe a perspective view of the portable incense burner 100 and details parts. The portable incense burner 100 comprises a hollow housing body (shaped-7) having a horizontal housing 17 attached to a vertical housing 10. The vertical housing 10 comprises a front vertical housing 21 which has a bottom curved end to mounted with the rear vertical housing 20 and the are a right and left vertical grill housing 19 attaching the two vertical front and rear housing 20 and 21. The horizontal housing 17 comprises a lower horizontal housing 22 attached from one end to the front vertical housing 21 forming a one part and an upper horizontal housing 23 attached to the lower horizontal housing and from one end to the rear vertical housing.

In the front end of the horizontal housing 17, there is a sliding incense tray 13 which has sliding removable tray 14 which is sliding out to be filled with incenses and closed by a plastic nozzle cover 15 which is locked by a snap-click holding the tray in its place. The body of the removable tray 14 has a metal part 16 to be heated and so the incense is heated but it has an insulated material between the metal part 16 of the removable tray 14 and the plastic nozzle cover 15 preventing heat transfers. The incense tray 13 housed over multi rips 28 attached inside the horizontal housing 17. These rips used to disperse heat.

Referring to FIGS. 3 and 4 and inside the horizontal housing 17, there is a circuit housing 24 which has a printed circuit board 36 made from a material that can handle operating temperature of 230° C., and spikes up to 240° C., two side frames 33 for fixing the printed circuit board inside the horizontal housing 17, a heater housing 29 housed in one end of the circuit board 36 beside the incense tray 13, a ripple surface 28 housed under the heater housing 29 for dispersing heat, a fan 30 housed in the other end of the circuit board 36 which used to direct the air flow towards incense tray 13 thought an air duct guide 32 and spreading incense smoke outside to the users, a double action trigger switch 41 housed in the printed circuit board 36 and connected to the hater housing 29 wherein the double action switch triggered by double action switch button 12 housed in the front vertical housing 21, and a DC battery charger socket 39 attached to the lower surface end of the circuit board 36 beside the fan for charging the recharging battery 25 housed in the vertical housing. There is a battery status LED 26 attached to the top end of the rear vertical housing 20 above the charging socket 39.

For preventing the heat from spreading to other parts of the printed circuit board 36, there is a line 40 of perforations acting as a heat barrier. This line housed in the circuit board PCB 36 beside the heater housing 29.

The heater 50 housed in the heater housing 29 and has a heater mounting body 44 which has a hole in its center for inserting a heater cartridge 42. The heater body 44 attached to the printed board 36 by a spring 43 attached to the body 44 from one end and to a hole in circuit board 36 for the other end. The spring 43 pushes the heater assembly 50 gently against the incense tray 13 so thermal contacts is ensured. The spring force is adjusted to preventing incense tray from pushing out. A thermistor can be integrated in the heater cartridge 42 or in the heater body 44 to monitor the heater temperature.

After turning the safety switch 11 ON housed in the front vertical housing 21, the user easily can start using the device by opening the nozzle cover 15 and place the incense bricks inside the tray 14 and close the nozzle cover 15 again, then the user must press the trigger switch button 12 lightly so the heater element 50 will be heated up with certain temperature and then the incense inside the tray 14 heated.

Pressing the trigger button 12 firmly activates the fan 30 which pull outside air 60 inside the air duct 32 through a surface air inlet 27 housed in the upper horizontal housing 23 and above the fan 30. The air forwards the tray 13 through the air duct guide 32 spreading incense smoke 61 outside to the users.

It is to be understood that the present invention is not limited to the embodiments described above, but encompasses any and all embodiments within the scope of the following claims.

The invention claimed is:

1. A portable incense burner comprising:
   a hollow housing body having a horizontal housing attached to a vertical housing;
   an incense tray attached to a front face of the horizontal housing;
   a circuit housing housed inside said horizontal housing;
   wherein the circuit housing comprising a printed circuit board (PCB), two side frames for fixing the printed circuit board (PCB) inside the horizontal housing, a heater housing housed in a first end of the circuit housing beside the incense tray, a ripple surface housed under the heater housing dispersing heat, a fan housed in a second end of the circuit housing, an air duct attached to the fan and elongated towards the second end of the circuit housing directing air flow towards the incense tray spreading incense smoke outside to a user, a double action trigger switch housed in the printed circuit board (PCB) and connected to the heater housing wherein the double action switch is triggered by a double action switch button housed in a front side of the vertical housing and a DC battery charging socket attached to an end of the printed circuit board (PCB) beside the fan for charging a recharging battery housed in the vertical housing.

2. A portable incense burner according to claim 1, wherein the vertical housing comprising a front vertical housing which has a bottom curved end to be mounted with a rear vertical housing;
   a right and left vertical grill housing attaching to the both the vertical front and the rear housing;
   wherein the horizontal housing comprises a lower horizontal housing attached from one end to the front vertical housing forming a one part and an upper horizontal housing attached to the lower horizontal housing and from one end to the rear vertical housing.

3. A portable incense burner according to claim 1, wherein the
   incense tray has a sliding removable tray which slides out to be filled with incenses wherein the sliding removable tray has a metal part to be heated and so the incense is heated, a plastic nozzle cover closing the incense tray, a snap-click lock holding the incense tray in a place and an insulated material housed between the metal part of the removable tray and the nozzle cover preventing heat transfers.

4. A portable incense burner according to claim 1, further having a heater housed in the heater housing, wherein the heater comprises:
   a heater mounting body having a hole in its center for inserting a heater cartridge; and
   a spring attached to the heater body from one end and to a hole in circuit board from the other end, wherein the spring pushes the heater gently against the incense tray so thermal contact is ensured and the spring force is adjusted preventing the incense tray from pushing out.

5. A portable incense burner according to claim 4, wherein the heater has a thermistor.

6. A portable incense burner according to claim 1, further having a battery status LED attached to a top end of the rear vertical housing above the charging socket.

7. A portable incense burner according to claim 1, wherein the printed circuit board (PCB) has a line for preventing heat from spreading to other parts of the printed circuit board wherein the line housed in the printed circuit board (PCB) beside the heater housing.

8. A portable incense burner comprising:
   a hollow housing body 7-shaped having a horizontal housing attached to a vertical housing;
   wherein the vertical housing comprising a front vertical housing which has a bottom curved end to be mounted with a rear vertical housing;
   a right and left vertical grill housing attaching to both the vertical front and the rear housing;
   wherein the horizontal housing comprises a lower horizontal housing attached from one end to the front vertical housing forming a one part and an upper horizontal housing attached to the lower horizontal housing and from one end to the rear vertical housing;
   a sliding incense tray attached to a front face of the horizontal housing;
   a printed circuit board (PCB) housed inside the horizontal housing;
   two side frames for fixing the printed circuit board (PCB) inside the horizontal housing;
   a heater housing housed in a first end of the printed circuit board (PCB) beside the incense tray;
   a ripple surface housed under the heater housing dispersing heat;
   a fan housed in a second end of the printed circuit board (PCB);

an air duct attached to the fan and elongated towards the second end of the printed circuit board (PCB) directing air flow towards the incense tray spreading incense smoke outside to a user;

a double action trigger switch housed in the printed circuit board (PCB) and connected to the heater housing wherein the double action switch is triggered by a double action switch button housed in a front side of the vertical housing; and a DC battery charging socket attached to an end of the printed circuit board (PCB) beside the fan for charging a recharging battery housed in the vertical housing.

9. A portable incense burner according to claim 8, wherein the sliding incense tray has a sliding removable tray which slides out to be filled with incenses wherein the sliding removable tray has a metal part to be heated and the incense is heated, a plastic nozzle cover closing the sliding incense tray which is locked by a snap-click holding the sliding incense tray in a place and an insulated material housed between the metal part of the removable tray and nozzle cover preventing heat transfers.

10. A portable incense burner according to claim 8, further having a heater housed in the heater housing, wherein the heater comprises:

a heater mounting body having a hole in its center for inserting a heater cartridge;

a spring attached to the heater body from one end and to a hole in circuit board from the other end, wherein the spring pushes the heater gently against the incense tray so thermal contact is ensured and the spring force is adjusted preventing the sliding incense tray from pushing out.

11. A portable incense burner according to claim 10, wherein the heater has a thermistor.

12. A portable incense burner according to claim 8, further having a battery status LED attached to a top end of the rear vertical housing above the charging socket.

13. A portable incense burner according to claim 8, wherein the printed circuit board (PCB) has a line for preventing heat from spreading to other parts of the printed circuit board wherein the line housed in the printed circuit board (PCB) beside the heater housing.

14. A portable incense burner according to claim 8, further comprising a surface air inlet housed in the upper horizontal housing and above the fan allowing the air entered to the fan which forwards the air to the tray through the air duct guide spreading incense smoke outside to a user.

* * * * *